United States Patent
Wieloch et al.

(10) Patent No.: US 7,605,911 B2
(45) Date of Patent: Oct. 20, 2009

(54) SYSTEM AND METHOD FOR VISUAL QUALITY CHARACTERIZATION OF HOLOGRAPHIC MATERIALS

(75) Inventors: Kelan Wieloch, Boothwyn, PA (US); Robert K. Grygier, Newark, DE (US)

(73) Assignee: Applied Extrusion Technologies, Inc., New Castle, DE (US)

( * ) Notice: Subject to any disclaimer, the term of this patent is extended or adjusted under 35 U.S.C. 154(b) by 184 days.

(21) Appl. No.: 11/870,125

(22) Filed: Oct. 10, 2007

(65) Prior Publication Data

US 2009/0097034 A1    Apr. 16, 2009

(51) Int. Cl.
*G01N 21/00* (2006.01)
(52) U.S. Cl. .................................... 356/73
(58) Field of Classification Search ........... 356/73
See application file for complete search history.

(56) References Cited

U.S. PATENT DOCUMENTS

| | | | |
|---|---|---|---|
| 4,998,785 A | 3/1991 | Ridout | |
| 5,615,005 A | 3/1997 | Valente et al. | |
| 5,629,068 A | 5/1997 | Miekka et al. | |
| 5,737,125 A | 4/1998 | Ohashi | |
| 5,742,432 A | 4/1998 | Bianco | |
| 5,756,183 A | 5/1998 | Kutsch et al. | |
| 5,932,150 A | 8/1999 | Lacey | |
| 6,120,710 A | 9/2000 | Makansi | |
| 6,677,029 B2 | 1/2004 | Wilkie | |
| 6,842,250 B2 * | 1/2005 | Schwarz ................. 356/445 |
| 7,157,135 B2 | 1/2007 | Decker et al. | |
| 2006/0154050 A1 | 7/2006 | Fitch et al. | |
| 2007/0091395 A1 | 4/2007 | D'Amato et al. | |

FOREIGN PATENT DOCUMENTS

| | | |
|---|---|---|
| JP | 04145341 A2 | 5/1992 |
| JP | 09196813 A2 | 7/1997 |

OTHER PUBLICATIONS

M.G.Moharam, et al., "Diffraction Characteristics of Photoresist Surface-relief Gratings", Applied Optics, vol. 23, No. 18, pp. 3214-3220, Sep. 15, 1984.
Edward F. Kelley, et al., "The Three Components of Reflection", Information Display, SID, Oct. 1998, pp. 24-29.
"Standard Practice for Obtaining Spectrometric Data for Object-Color Evaluation" ASTM International, Pub. No. E1164-02, pp. 882-889, United States.

(Continued)

*Primary Examiner*—F. L Evans
(74) *Attorney, Agent, or Firm*—Caesar, Rivise, Bernstein, Cohen & Pokotilow, Ltd.

(57) ABSTRACT

Apparatus and method for characterizing perceived visual quality of holographic materials, such as diffraction gratings. A white light source directs a collimated beam onto an embossed material. The first order diffracted light strikes a white background directly in view of a digital camera, which records an image. The image is analyzed to calculate total color intensity of the diffracted light and an estimate of the color distinctness. The data is compared to other samples to determine relative visual quality.

13 Claims, 6 Drawing Sheets

OTHER PUBLICATIONS

"Standard Test Method for Coefficient of Retroreflection of Retroreflective Sheeting Utilizing the Coplanar Geometry", ASTM International, Pub. No. E810-01, pp. 848-856, United States.

Andrew Gardner, et al., "Linear Light Source Reflectometry", University of Southern California Institute for Creative Technologies Graphics Laboratory, ACM SIGGRAPH 2003 Conference, Marina del Rey, California.

Guylain Lemelin, et al., "Holographic Imaging of 3D Object on Dichromated Polymer Systems", Pure Applied Optics, vol. 5, 1996, p. 95-103, printed in the UK.

A.S.Litvinenko, et al., "The Device of Measurement of Parameters of Holograms", Proceedings from Laser and Fiber-Optical Networks Modeling, Sep. 2004, 6th International Conference in Kharkav, Ukraine, pp. 302-304.

* cited by examiner

SYSTEM AND METHOD FOR VISUAL QUALITY CHARACTERIZATION OF HOLOGRAPHIC MATERIALS

FIELD OF THE INVENTION

This invention relates to techniques for evaluating visual appeal of holographic materials.

BACKGROUND OF THE INVENTION

Holographic materials can be used for functional light management or for decoration. Decorative holographic materials make for appealing or eye catching displays. These materials are used for labels, boxboard lamination, flexible packaging, or other display or decorative applications. The appeal comes from light diffraction induced by a grating pattern either on the surface or buried in a lamination. Examples of holographic materials used for functional light management include diffraction gratings for monochrometers, retroreflective materials for enhanced road sign visibility, and holographic protective elements for security tags.

When incident light strikes the surface of a holographic material, it can be directed in one or more of five possible modes: transmission, absorption, direct reflection, diffraction and scatter. Transmission is the light that passes through the material without changing direction. Absorption is the light that is retained by the material. Direct reflection is the light that is returned at an equal and opposite angle to the incident light. Diffracted light is the light that is reflected or transmitted in discrete directions due to mutual interference mediated by periodic structures. Scatter is all light that is redirected irregularly including retroreflection, redirection from surface plasma polaritons, haze, surface roughness or imperfections, and Lambertian reflection. A description of the characteristics of surface relief diffraction gratings is found in M. G. Moharam et al, "Diffraction Characteristics of Photoresist Surface-relief Gratings" 23 Applied Optics 3214 (Sep. 15, 1984). A description of the components of reflection is found in Edward F. Kelley, et al. "The Three Components of Reflection" in Information Display, SID October 1998 pp. 24-29. Discussion of measurement of the color of objects is found in "Standard Practice for Obtaining Spectrometric Data for Object-Color Evaluation" ASTM Int'l pub. no. E1164-02. Discussion of methods for measuring retroreflective material is found in "Standard Test Method for Coefficient of Retroreflection of Retroreflective Sheeting Utilizing the Coplanar Geometry" ASTM Int'l pub. no. E810-01. All of the references stated herein are incorporated by reference.

Perceived visual quality of a holographic material has two components: Color intensity and color distinctness. Color intensity is the amount of diffracted light relative to the amount of incident light, or the diffraction efficiency. This is analogous to value in the hue, saturation, value (HSV) color model. In the case of surface relief patterns, color intensity can be theoretically modeled based on the depth, periodicity and shape of the surface relief pattern and the overall reflectivity of the surface. However, models are often very complex and can miss key features that may affect diffraction intensity such as surface plasma polaritons. Color distinctness is the sharpness of the colors or the color saturation. This is analogous to color saturation in the HSV color model. A holographic material can have good color intensity but have low perceived visual quality because the color distinctness is low. Light that is scattered by the sample reduces the distinctness of the colors. A holographic material will have a high perceived visual quality if it has high color intensity and high color distinctness.

Visual quality of a holographic material is an important property that is generally not measured or controlled. A common practice to determine the perceived visual quality is to perform a manual inspection with a trained observer. This subjective approach includes irregularities owing to factors such as lighting conditions, material orientation, and the observer's experience, mood or preferences. An automated, repeatable measurement process is desirable in order for manufacturers to produce consistent products.

An article written for the ACM SIGGRAPH 2003 Conference, Andrew Gardner et al., "Linear Light Source Reflectometry" describes a technique to estimate spatially varying reflectance properties of a surface based by taking a series of digital photographs of the surface while the surface is being illuminated with a single pass of a linear light source. This allows measurement of the diffuse color, and specular color of each point of the surface. A laser light source is also used to measure surface roughness. The article does not disclose a method or system for measuring perceived visual quality of a holographic material.

U.S. Pat. No. 5,615,005 discloses an instrument for grading gemstones. The device illuminates a gemstone with a plurality of light frequencies and measures an image of the gemstone illuminated at each frequency with a Charge Coupled Device (CCD) to obtain the spectral response of the gemstone.

An article in Pure Applied Optics by Lemelin et al. entitled "Holographic imaging of 3D objects on dichromated polymer systems", vol. 5, 1996, pages 95-103, describes a method to measure the diffraction efficiency of a hologram using laser light.

Proceedings from Laser and Fiber-Optical Networks Modeling, September 2004, $6^{th}$ International Conference in Kharkav, Ukraine by Litvinenko et al. entitled "The device of measurement of parameters of holograms" describes a method to measure the diffraction efficiency of a hologram Patents in the field of holographic materials and/or diffraction grating include: U.S. Pat. Nos.: 7,157,135; 6,677,029; 6,120,710; 5,932,150; 5,756,183; 5,742,432; 5,737,125; 5,629,068 and 4,998,785, Japanese patents JP 09 196813 A and JP 04 145341 A, and U.S. published patent applications: US2006-0154050 and US2007-0091395. Also in the field are co-pending U.S. patent application Ser. No. 11/683,209: System and Method for Making Seamless Holograms, Optically Variable Devices and Embossing Substrates, filed Mar. 7, 2007 and Ser. No. 11/678,918, filed Feb. 26, 2007 Method for Optical Characterization and Evaluation of Optically Variable Devices and Media, filed Feb. 26, 2007. The prior art has not disclosed a method or instrument for characterizing visual quality of holographic materials. Having an instrument to characterize visual quality eliminates bias and provides acceptance criteria so that consistent reproducibility can be maintained.

SUMMARY OF THE INVENTION

In an exemplary embodiment, the invention provides a method for evaluating a holographic material. The method includes the steps of directing light from a light source onto the holographic material; performing a measurement of the diffracted light; performing a measurement of the scattered light; and comparing the measurement of the diffracted light and the measurement of the scattered light to measurements for like holographic materials. In an embodiment, the light source is a collimated white light source. In a further embodiment, the diffracted light is projected onto a scattering surface and the light projected onto the scattering surface is measured using a CCD. An analysis is made of the image made by the CCD.

Other advantages and novel features of the invention will become apparent to those skilled in the art upon examination of the following detailed description of a preferred embodiment of the invention and the accompanying drawings.

DESCRIPTION OF THE PREFERRED EMBODIMENT OF THE INVENTION

The system disclosed herein provides a method and a tool to measure and quantify the perceived visual quality of holographic materials. In a typical embodiment, the system addresses the above-described needs and limitations by directing light onto a holographic material such that diffracted and scattered light is directed onto a surface removed from the holographic material, capturing some of the diffracted and scattered light, and analyzing the captured light.

Figure 1:
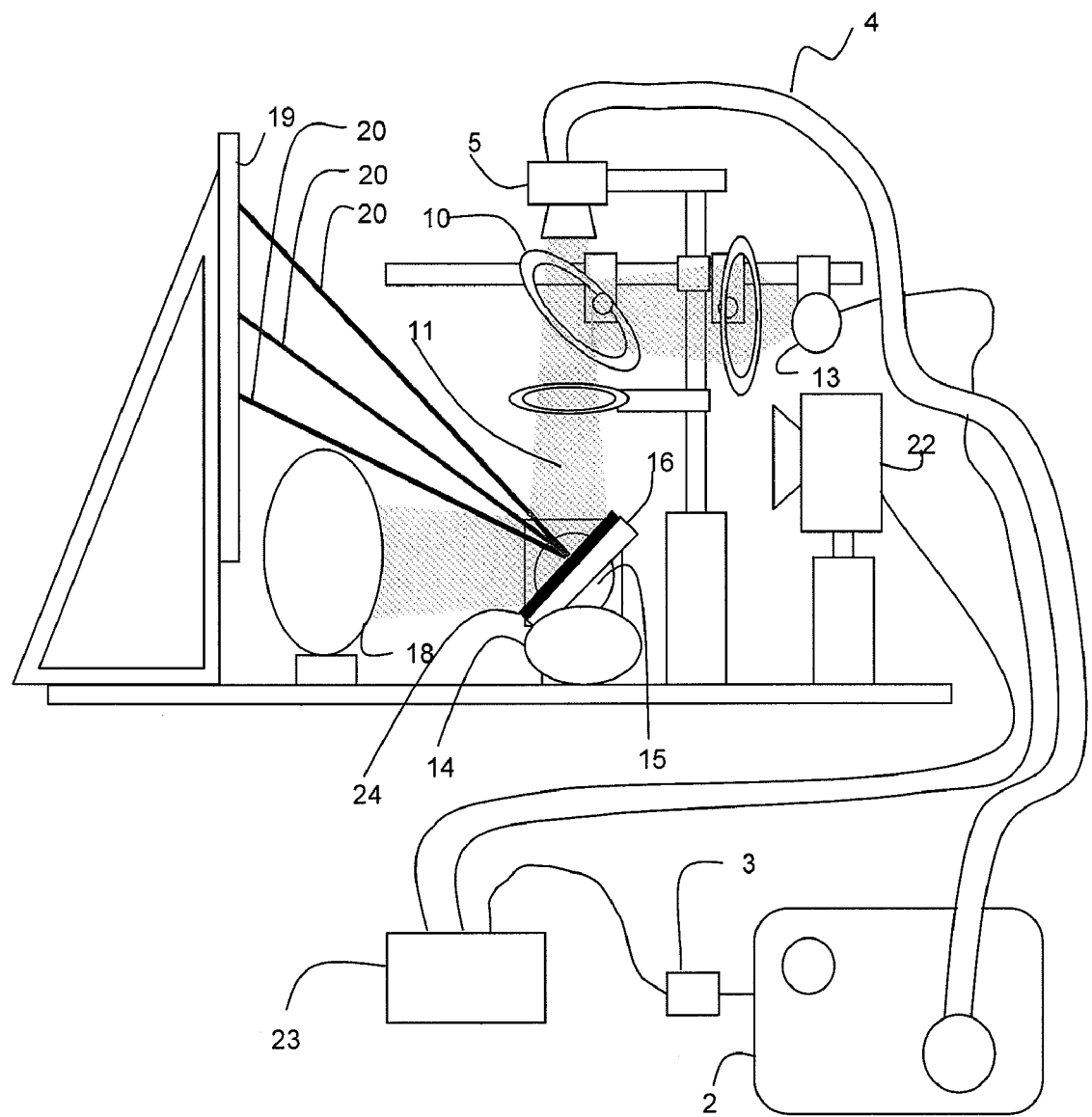
FIG. 1 is a diagram of an exemplary system for measuring visual quality of a holographic material.

Referring now to various figures of the drawings wherein like reference characters refer to like parts, there is shown in FIG. 1, a block diagram of an exemplary embodiment of a system for evaluation and characterization of holographic materials.

Shown in FIG. 1 is a light source 2, which creates a collimated beam of white light from an incandescent bulb. In an exemplary embodiment, the bulb has a color temperature of 3250K. Other light sources can be used such as fluorescent bulbs, incandescent bulbs with other color temperatures, or fully or partially polarized light. A while light source has the advantage of illuminating the holographic material with a wavelength spectrum typical for how an observer would see the holographic material. An exemplary light source is a Dolan-Jenner Fiber Optic Illuminator, Model DC-950. The light is transferred from the light source 2 to a focusing lens 5 through a light guide 4. In an embodiment, the light guide is a fiber optic cable. The focusing lens 5 is preferably stationary, but it can be moved about the sample to change the incident angle. The focusing lens 5 and light guide 4 are not needed if the beam of light 11 from the light source is sufficiently collimated. In an embodiment, preferably, the highest possible degree of collimation is used. In an embodiment, the light beam 11 is directed through a beam splitter 10, where part of the light is directed toward a sensor 13 to monitor the intensity of the light beam 11. The light intensity signal from the sensor 13 is fed back to a computer 23, which then directs a digital to analog converter 3 to produce a signal that adjusts light source 2 so as to control light intensity and correct for variations in intensity from effects such as bulb fade, temperature or other reductions to light intensity. Preferably, the remainder of the light exiting the beam splitter 10 is undisturbed until it hits the sample 24. In various embodiments, the light beam 11 can be focused, defocused, wavelength filtered, polarized, expanded, condensed, unpolarized or even masked. The light projected onto the sample 24 is large enough to cover a representative area for a quality measurement but small enough to minimize angular effects from beam size, beam diversion or loss of light intensity. In an embodiment, the projected light is preferably free of optical effects such as a penumbra and has very limited beam divergence or convergence, of less than 20°. Using a small diameter fiber optic cable and high quality optical components minimizes these effects.

The sample holder 16 fixes the location of the sample. This can be at any angle to the incident light as long as the entire beam strikes the surface of the sample 24 and the desired diffracted light is directed to the flat surface 19 which scatters it so a detector 22 can image this diffracted light. In an embodiment, the sample holder 16 can be tilted on a stage 15 to adjust for the diffraction angle. The sample 24 may also be spun (during or prior to testing) or rotated on any axis. The sample can also be adjusted to view other diffraction orders such as the −1st order in case it is different from the 1st order, the 0th order, or the +/−2nd or higher orders. The sample holder 16 is preferably optically clear behind the sample so any transmitted light can be controlled, preferably collected with a beam dump 14. Reflected light is collected with a beam dump 18. In another embodiment, instead of a beam dump 14, a separate detector measures light transmission through the sample 24. In another embodiment, the directly reflected light is measured with a separate detector.

In an exemplary embodiment, the diffracted light 20 is made to strike a flat surface 19, which scatters it. A detector 22 images the scattering surface 19 and records an image. The scattering surface 19 is not required if the light 20 is diffracted directly into the detector 22. Preferably, the scattering surface 19 is a flat calibrated white background, free of defects or light absorbing materials with a uniform spectral reflectivity. Preferably, the detector 22 is a CCD camera with color filters for red, green and blue components. The detector does not have to be a CCD array; it can be a single detector, a line detector a CMOS chip or any other photo diode, provided that the diffracted light is in some way distinguished from scattered light. The diffracted light 20 can be focused, filtered, polarized, unpolarized, expanded, condensed, split or scattered prior to detection. The location of the detector 22 can be placed anywhere that light is diffracted. For viewing other diffraction orders, the sample 24 can be rotated, the incident light source moved, or the detector 22 can be moved to different locations.

The components are preferably black to absorb stray light. Enclosing the components reduces stray light, as does dimming the lights in the area of testing. The entire unit can be built in a horizontal or vertical position, or even diagonal, which may be more practical for ease of operation, reliability, assembly or maintenance.

Figure 2:
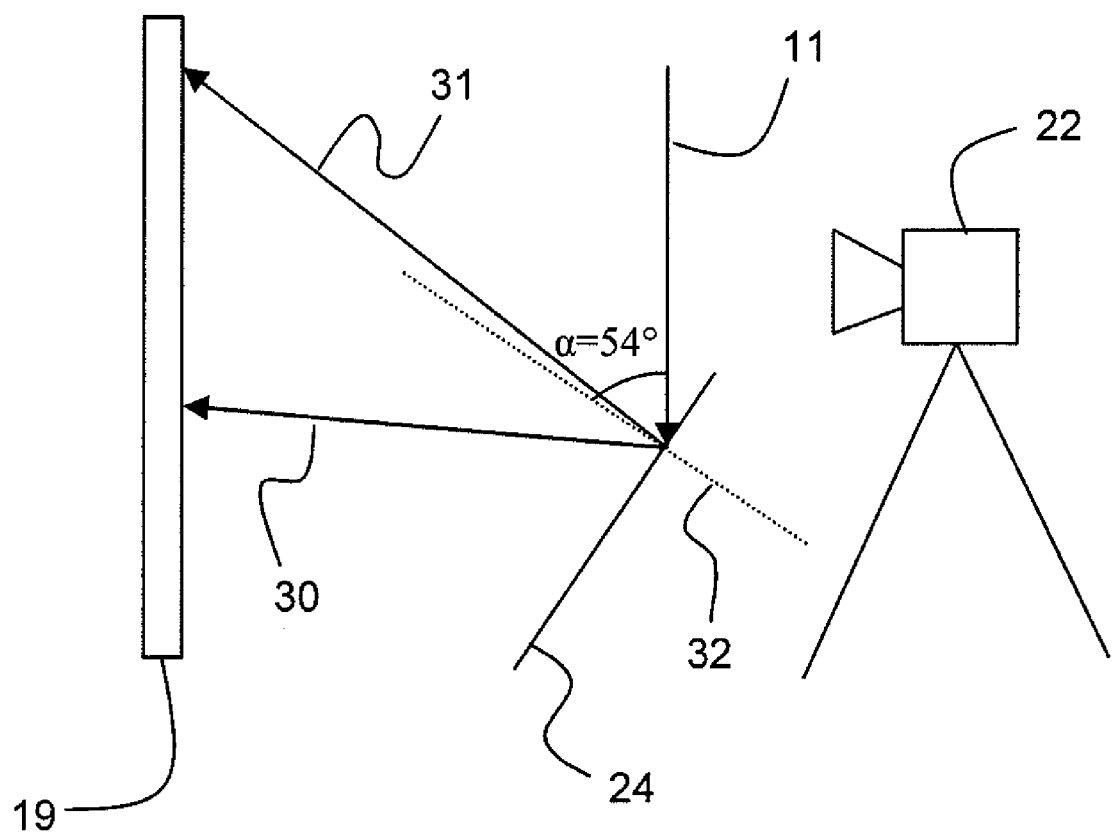
FIG. 2 is a block diagram of an exemplary system for measuring visual quality of a holographic material.

FIG. 2, shows a simplified block diagram illustrating the proper angular positioning of the sample 24. In an exemplary embodiment, the sample 24 is held such that a line normal to its surface is approximately 54° to the incident light. This angle ensures that all the visible light will be projected onto the white background 19 regardless of the pattern on the holographic material 24. The projection angle for gratings having spacing (d) is calculated using the grating equation:

$m\cdot\lambda = d\cdot(\sin\alpha + \sin\beta)$

Where α is the incident light angle (from the surface normal 32) and β is the angle of the diffracted light (from the surface normal 32). For embodiments that capture only the 1st order diffraction, m=1. λ ranges from 380 nm to 730 nm (range of human vision), and, in an exemplary embodiment covering a range of sample grating depths, d ranges from 880 nm to 1500 nm. The highest and lowest angles are β=−34° (380 nm light with d=1500 nm) and β=1° (730 nm light with d=880 nm). These are depicted as light rays 31 and 30 respectively in FIG. 2. These angles allow the camera 22 to be normal to the white background 24 so there are no geometric adjustments needed.

Figure 3:
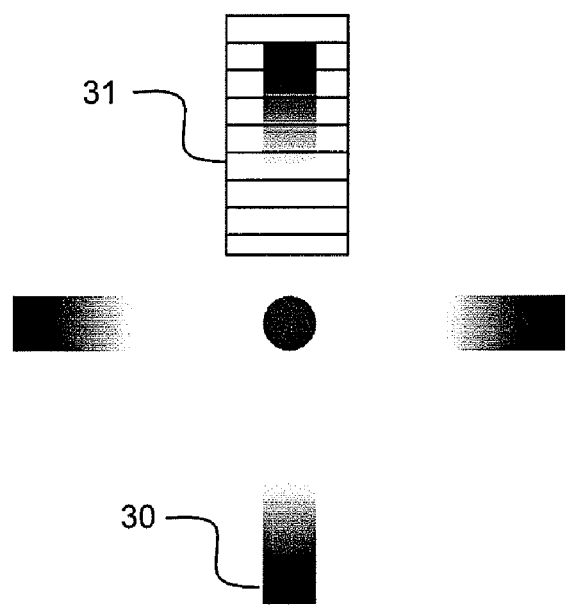
FIG. 3 is a diagram of a diffraction pattern for a grating that diffracts light in two directions.
Figure 4:
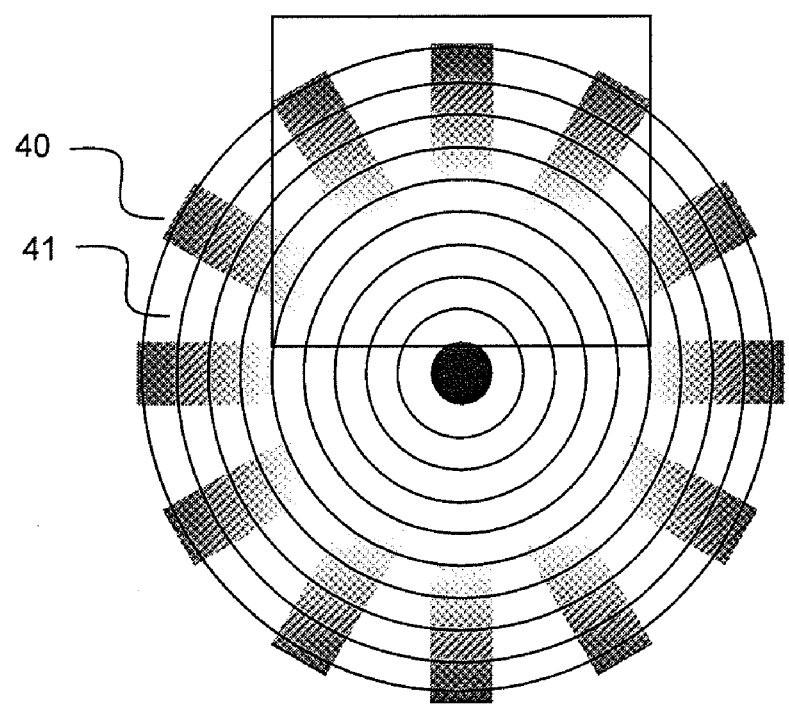
FIG. 4 is a diagram of a diffraction pattern for a grating that diffracts light in more than two directions.
Figure 5:
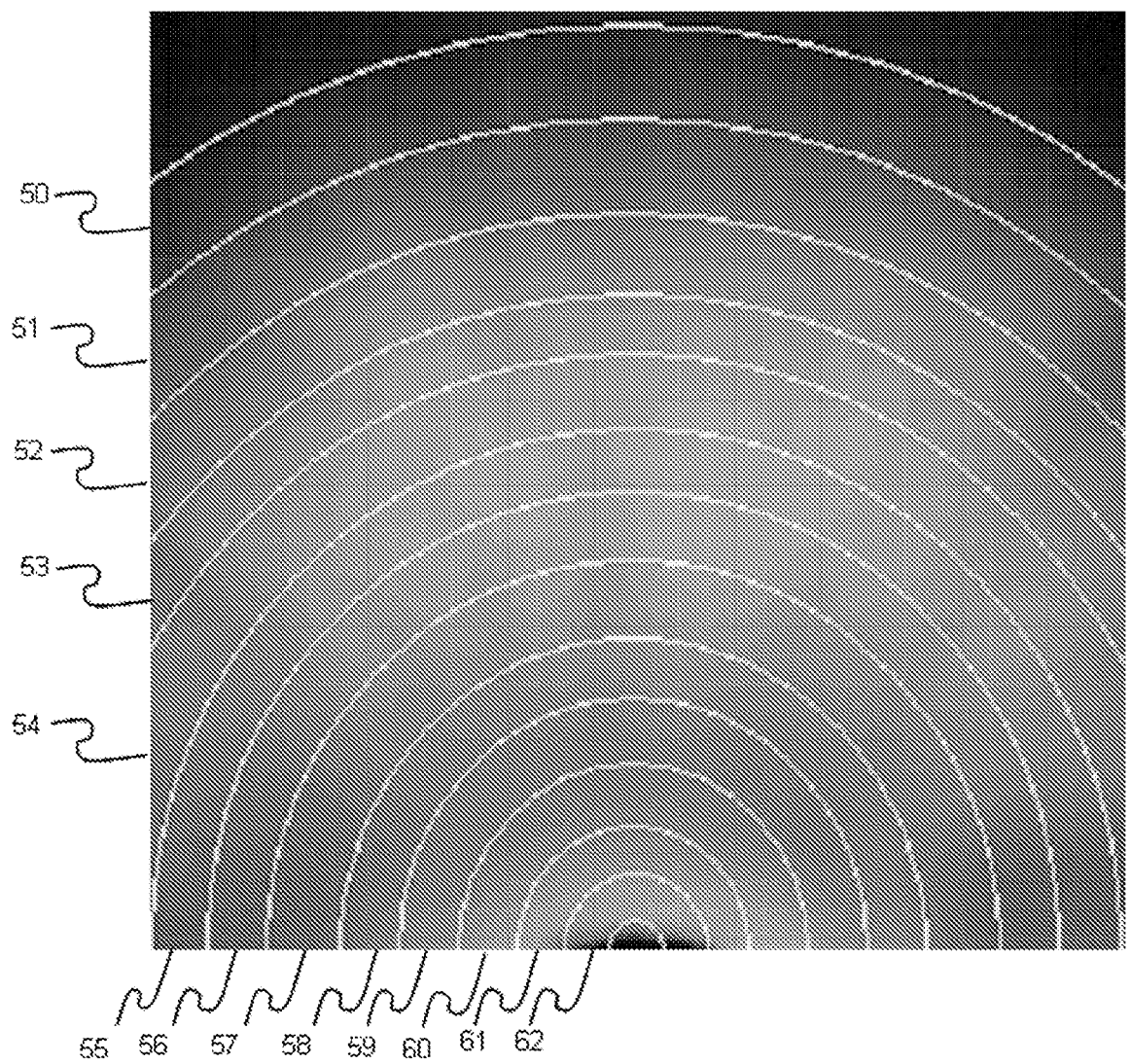
FIG. 5 is an image of a diffraction pattern broken into annular elements.
Figure 6:
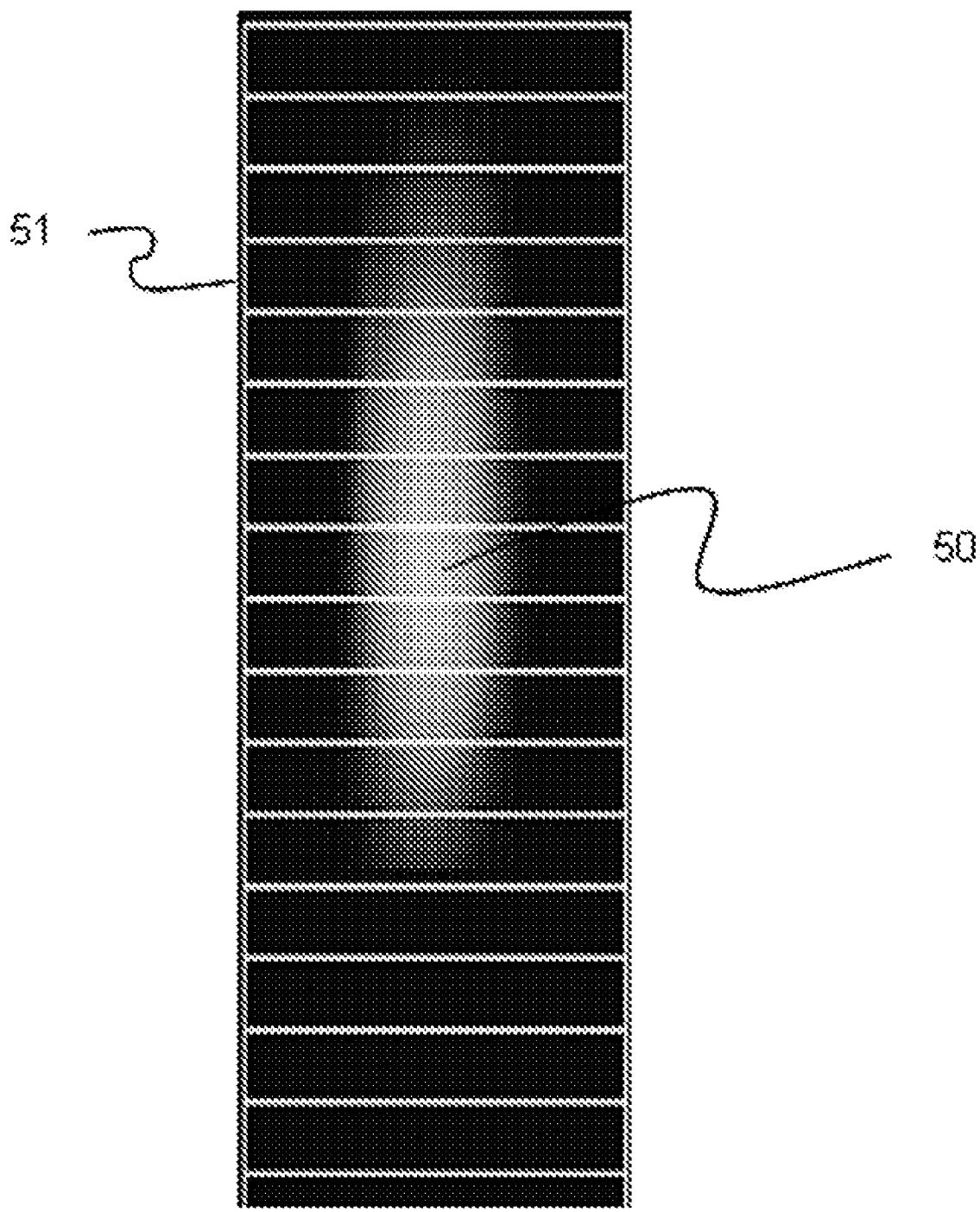
FIG. 6 is an image of a diffraction pattern broken into rectangular elements.

The collected light must be analyzed to determine both the color intensity and the color distinctness. There are several ways to determine the color intensity. One method is to analyze an image captured by a CCD, where the intensity level of each pixel in the image of the diffracted light is summed. In an exemplary embodiment, an image of the $1^{st}$ order diffraction is made and separated into a plurality of finite elements, wherein the elements are positioned to correspond to small wavelength ranges. A typical embodiment uses ten or more elements. As shown in FIG. 3, for simple holographic patterns that produce diffraction 30 in two directions, the finite elements 31 can be rectangles, as illustrated. As shown in FIG. 4, for holographic patterns that diffract light in a large number of directions 40, an exemplary embodiment uses finite elements that are radial annuli 41, centered at the location of the direct reflection. An example of a diffraction image broken into 14 annular elements (50-62) is shown in FIG. 5. An example of a simple diffraction image 50 such as is shown in FIG. 3, broken into rectangular elements 51 is shown in FIG. 6. In embodiments where the detector 22 filters the diffraction image into separate red, green and blue components, the intensity of each color in each finite element may be summed separately. The sum totals for each finite element must be corrected for size. For the example shown in FIG. 5, there are two size correction factors: one is based on the radius of the annulus and one is based on the segment size of the annulus relative to the entire annuli.

Figure 7:
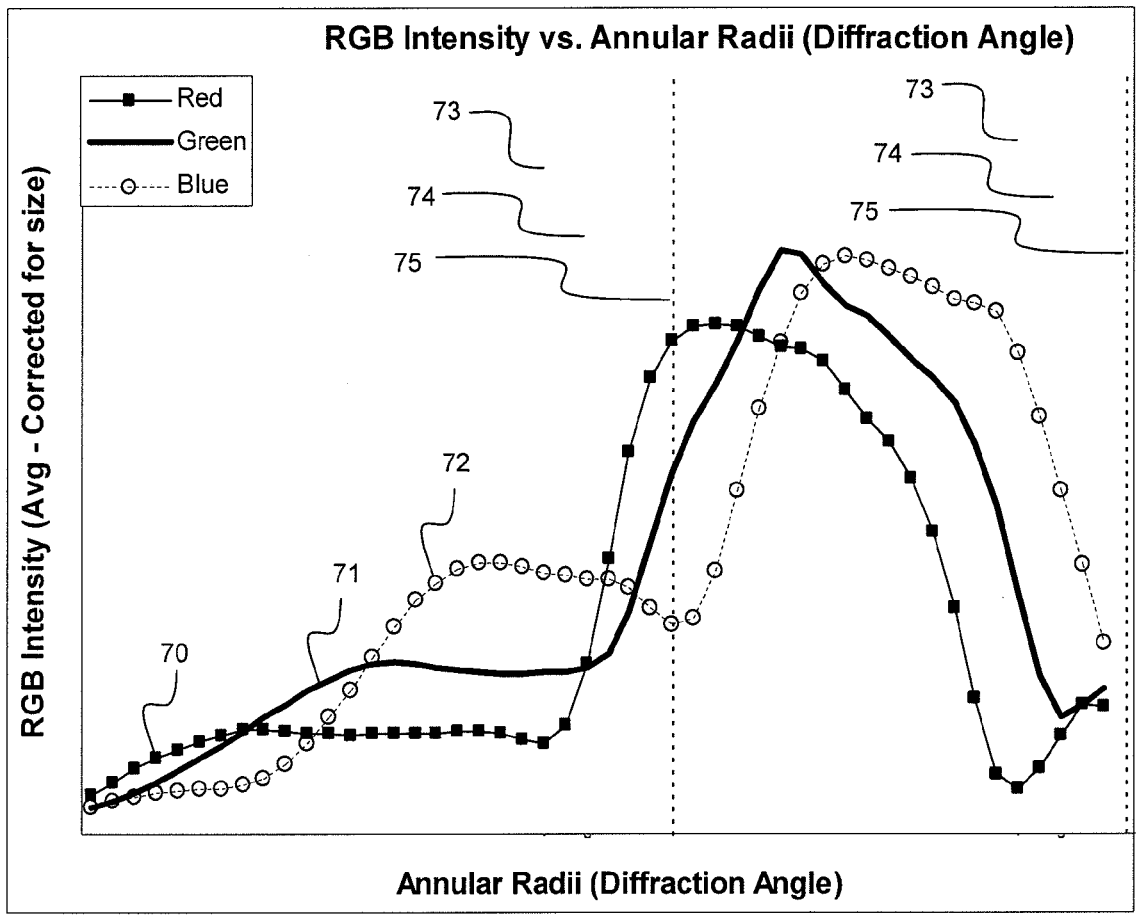
FIG. 7 is a graph of Red, Green Blue (RGB) intensity versus annular radii for an image such as that shown in FIG. 5.

In a further embodiment, the sum totals of each color component (red, green and blue) for each element are graphed versus the annulus radii. An example graph is shown in FIG. 7. This is analogous to the color components (red, green and blue) plotted against diffraction angle. The integration of these lines corresponds to the color intensity. Integration limits exclude points that contain mostly $0^{th}$ order reflection, scattered light or $+/-2^{nd}$ order diffraction or higher orders. Typically these are determined by minimums in the graphs that occur between the direct reflection and the $1^{st}$ or $-1^{st}$ order and then again between the $1^{st}$ and $2^{nd}$ order diffraction or between the $-1^{st}$ and $-2^{nd}$ order diffraction. The integration can also be performed by fitting a Gaussian curve to the $1^{st}$ or $-1^{st}$ order diffraction peak. Note truncation limits 70, 71 and 72 as shown in FIG. 7, which are applied to the red 73 green 74 and blue 75 curves respectively. The remaining points within each of the truncation limits are integrated to give a total color intensity value.

One method to determine color distinctness is to integrate the finite elements that do not contain a significant portion of $0^{th}$ order or any diffraction order ($+-/1^{st}$ order, $+/-2^{nd}$ order or higher orders). Another method to determine color distinctness is to look at the minimum value of each red, green and blue component located between the direct reflection and the $1^{st}$ order or $-1^{st}$ order diffraction. A low minimum value or a low total integration corresponds to a high color distinctness.

Still another method for collecting the image is to collect all the diffracted light (including $1^{st}$ and $-1^{st}$ orders) with a CCD array. This gives more accurate results since the $1^{st}$ and $-1^{st}$ orders may be different.

In cases where the wavelength of light of discrete elements of the collected image is known or can be determined, corrections can be made to correspond to the response of the human eye to various wavelengths. Since the measure of perceived visual quality is ultimately a human response, this correction is useful. Frequently digital cameras have this correction built in.

Once the color intensity and the color distinctness values are determined, perceived visual quality is a function of those two values. The highest visual quality is characterized as having the highest color intensity and high color distinctness. One method to determine visual quality is to subtract the color distinctness value from the color intensity. Other methods to determine visual quality can be used.

Without further elaboration, the foregoing will so fully illustrate this invention that others may, by applying current or future knowledge, readily adopt the same for use under various conditions of service.

We claim:

1. A method for characterizing the perceived visual quality of a holographic material, which, when illuminated, produces diffracted light and scattered light, the method comprising:
    directing light from a collimated white light source onto the holographic material;
    performing a measurement of the diffracted light;
    performing a measurement of the scattered light; and
    comparing said measurement of diffracted light and measurement of scattered light to measurements for like holographic materials.

2. The method of claim 1, wherein said measurement of diffracted light is a measurement of first order diffracted light.

3. The method of claim 1, further comprising the steps of directing a portion of the diffracted and the scattered light onto a surface;
    creating an image of said surface with a CCD array; said image representing light intensity, and measuring a portion of said image to perform said measurements of the diffracted light and the scattered light.

4. The method of claim 3, wherein said image comprises red, green and blue images and said measurements are performed separately for each of said red, green and blue images.

5. The method of claim 3 wherein said image of said surface is broken into a plurality of elements and each element is measured to perform said measurements of the diffracted light and the scattered light.

6. The method of claim 5, wherein said plurality of elements is comprised of sections of annular elements.

7. The method of claim 5, wherein said plurality of elements is comprised of rectangular elements.

8. A method for characterizing the perceived visual quality of a holographic material, which, when illuminated, produces diffracted light and scattered light, the method comprising:
    directing light from a collimated white light source onto the holographic material;
    projecting the diffracted and the scattered light onto a scattering surface;
    creating an image of the diffracted and scattered light projected onto a scattering surface;
    measuring said image to produce a measurement of the diffracted light and a measurement of the scattered light; and comparing said measurement of diffracted light and measurement of scattered light to measurements for like holographic materials.

9. The method of claim 8, wherein said image is created with a CCD.

10. The method of claim 8, wherein said image is created of red, green and blue components of said light projected onto a scattering surface.

11. An apparatus for characterizing the perceived visual quality of a holographic material which, when illuminated, produces diffracted light and scattered light, comprising:

a white light source to produce a collimated light beam;

a scattering surface; and a light measurement device, wherein said collimated white light beam is directed to the holographic material, the diffracted light and the scattered light are projected onto said scattering surface and said light projected onto said scattering surface is measured with said light measurement device.

12. The apparatus of claim 11, wherein said light measurement device is a CCD.

13. The apparatus of claim 12, wherein said CCD creates an image of said light projected onto said scattering surface, said image comprised of a plurality of pixels, said pixels consisting of pixels representing red, green and blue components of said projected light and said measurement of light projected is performed separately for said red, green and blue components.

* * * * *